United States Patent [19]

Bossard et al.

[11] Patent Number: 4,711,118

[45] Date of Patent: Dec. 8, 1987

[54] DETECTION OF WATER ENTRAPPED IN ELECTRONIC COMPONENTS

[75] Inventors: Peter R. Bossard, Langhorne, Pa.; John A. Mucha, Madison, N.J.

[73] Assignee: American Telephone and Telegraph Company, AT&T Bell Laboratories, Murray Hill, N.J.

[21] Appl. No.: 318,330

[22] Filed: Nov. 5, 1981

[51] Int. Cl.[4] ........................ G01N 21/00; G01M 3/00
[52] U.S. Cl. ........................................... 73/73; 73/52; 356/256
[58] Field of Search ............... 73/52, 29, 73, 336.5, 73/1 G; 340/602, 604; 250/574, 573, 576

[56] References Cited

U.S. PATENT DOCUMENTS

| | | | |
|---|---|---|---|
| 2,412,192 | 12/1946 | Agnew | 73/52 |
| 2,621,297 | 12/1952 | Obermaier | 73/29 |
| 2,749,744 | 6/1956 | Doudera | 73/52 |
| 3,636,768 | 1/1972 | Tinet | 73/29 |
| 4,056,966 | 11/1977 | Ketelsen | 73/1 G |

*Primary Examiner*—Daniel M. Yasich
*Attorney, Agent, or Firm*—Bruce S. Schneider

[57] ABSTRACT

The accuracy of measurements made to determine the extent of water vapor trapped upon encapsulation of an electronic device is significantly enhanced by carefully controlling the measurement technique employed. In particular, the encapsulant is generally punctured and the water vapor thus released is monitored. It has been found that to obtain an accurate measurement of the magnitude of the water vapor released, this measurement must be made within 0.1 second of the time of encapsulant punctured and released into a glass system. By using an absorption technique with suitable electronics, this time requirement is fulfilled and significantly more accurate quantitative measurements of entrapped water vapor are obtained.

6 Claims, 4 Drawing Figures

DETECTION OF WATER ENTRAPPED IN ELECTRONIC COMPONENTS

BACKGROUND OF THE INVENTION

1. Field of the Invention

This invention relates to the fabrication of electronic components and in particular the quality control of such fabrication.

2. Art Background

Generally, after integrated circuits and other electronic devices, such as discrete field effect transistors are produced, they are encapsulated in materials such as ceramics, metals and plastics. This encapsulation protects the device from the atmosphere and from abrasion. However, during the encapsulation it is almost inevitable that some water vapor is trapped between the encapsulant and the encapsulated device. If an excessive amount of water is trapped, the device generally will degrade to an unacceptable level through mechanisms such as corrosion or inducement of abnormal leakage currents in the device. Therefore during device manufacture, one quality control procedure is to measure the entrapped water in a representative sampling of devices from a batch of devices to ensure that this representative group of one or more devices, and by inference the entire batch, does not have an excessive amount of trapped water.

Generally a large number of techniques are available for detecting water vapor in continuous fluid flow and large gas volumes. flow and large gas volumes. (See Wexler, Arnold, ed., "Humidity and Moisture: Measurements and Control In Science & Industry," Reinhold Publishing Corp., (New York, 1965) for a review of available measurement methods including infrared techniques.) However, for device quality control purposes involving small encapsulated volumes, the conventional method of measuring water vapor levels employs mass spectrometry. In this technique, the encapsulant layer of the sample device is punctured in a vacuum chamber to release the trapped water vapor. An inlet to a mass spectrometer such as a quadrupole spectrometer is positioned in proximity to the punctured area of the encapsulated device. The released water vapor is thus sampled and a measure of the water vapor is made by integrating the amount of water detected over a period of time. Typically, on a mass spectrometric apparatus, the time period over which the amount of detected water vapor is integrated is arbitrarily chosen. (See R. W. Thomas, "Moisture, Myths, and Microcircuits," *IEEE Transactions On Parts, Hybrids and Packaging*, PHP-12, pp. 167–171 (1976) for a review of mass spectrometric quality control measures.)

Although the mass spectrometric method is widely practiced, the results obtained are not entirely satisfactory. The difficulties in mass spectrometric analysis are emphasized by the numerous literature references indicating that tremendous care is required to maintain consistent results for such mass spectrometric measuring of water vapor content in devices. Indeed, studies have indicated that the correlation between measurements of controlled samples on different equipment have yielded a large scatter in the measured values of the water vapor. (See R. W. Thomas and D. E. Meyer, "Moisture In SC Packages," *Solid State Technology*, 17, pp. 56–59 (1974) and K. L. Perkins, "Moisture Measurement Studies," *Semiconductor Measurement Techniques and Reliability Techniques for Cardiac Pacemakers*, pp. 60–65 NBS Special Publication 400-50, US Government Printing Office (1978).) Thus, two devices which potentially can undergo substantially different levels of degradation may well be incorrectly analyzed by conventional techniques to be both within acceptable quality control levels.

SUMMARY OF THE INVENTION

It has been found that to measure encapsulated water vapor accurately and consistently, the integrated measurement, i.e., the measurement made to sense the effect of all the water molecules present in the sample, should be made during a time period which is extremely short compared to integration times employed in mass spectrometric quality control measures. Specifically, the time elapsed between the time of device puncture and the integrated measurement of the data needed to determine the water vapor level should be short compared to the time required for substantial adsorption of water on, or desorption of water from, the walls of the measuring apparatus. Further, this time period criterion is satisfied and is easily determined by first making a measurement of the water vapor present in a small volume, i.e., less than 1 cc, sample taken from a continuously flowing gas stream. This result is compared to a similar measurement made on the continuous gas flow when the amount of this gas flow introduced continuously through the measurement chamber is controlled to produce the same total pressure as was present in the chamber during the measurement of the small volume sample. The time period of the measurement technique is sufficiently short if the value obtained for the continuous flow measurement is within 20 percent of the value obtained during the measurement of the small volume sample. A spectroscopic absorption technique has been found particularly suitable for making measurements within this relatively short time period. By using the inventive technique, reproducible quantitative results are attained.

DETAILED DESCRIPTION

The inventive quality control technique involves the rapid measurement of the level of water vapor after puncturing of the device encapsulating layer. It has been found that even when the walls of the equipment are heated, substantial water vapor adsorption on these walls occurs. Therefore, the measurement should be taken in a time period after puncturing of the test device that is short compared to the time for substantial adsorption of water vapor on, or desorption of water from, the walls of the equipment. It is easy to determine whether a given measurement satisfies this criterion by first making a measurement of the water vapor present in a small volume sample taken from a continuously flowing gas stream. This result is compared to a similar measurement made on the continuous gas flow where the amount of this gas flow introduced continuously through the measurement chamber is controlled to produce the same total pressure as was present in the chamber during the measurement of the small volume sample. If the continuous flow measurement yields a value that is within 20 percent of the measurement made on the small volume sample, then the time period criterion is satisfied. (For even more accurate results it is desirable that the values agree within 10 percent, preferably 5 percent.) For example, in a glass-walled measuring apparatus, if the measurement is not made within 0.1 second, preferably within 10 milliseconds, of the time of release of the entrapped water, errors (systematic undervaluation) in the quantitative measurement of the water are made. As discussed below, an absorption spectroscopic technique is particularly suitable for making such rapid measurements.

Although the invention involves the realization that the measurement should be performed within the time scale previously discussed, for pedagogic purposes it will be described with reference to a spectroscopic absorption technique that is particularly adapted to allow such measurements. Other measurement techniques with suitable response are also contemplated to be within the invention. However, it should be noted that presently available mass spectrometric techniques applied to device quality control, although potentially suitable for making such measurements, have been applied in a manner which does not allow satisfaction of the desired time criterion.

Figure 1:
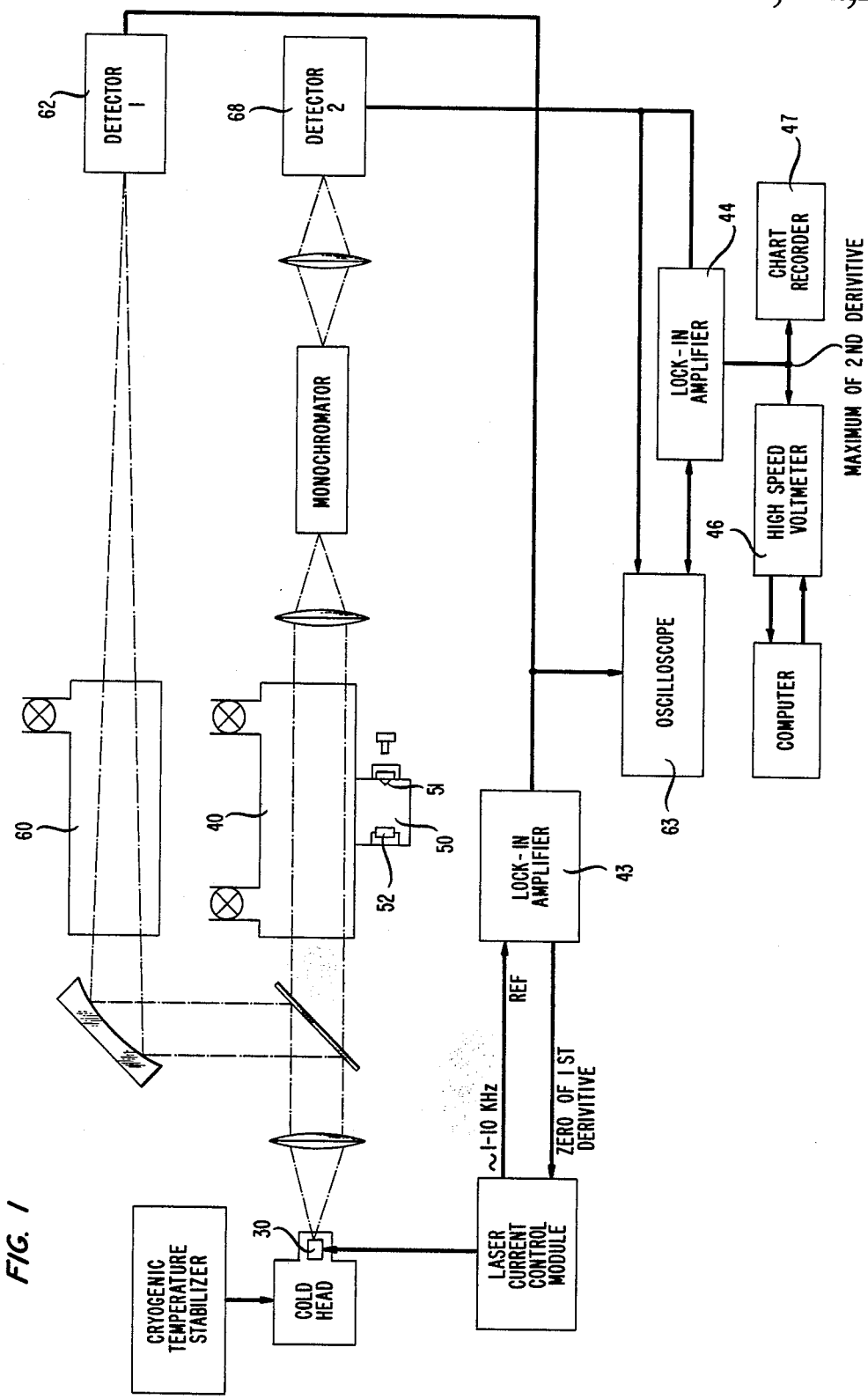
FIG. 1 is a schematic representation of an apparatus suitable for practicing the subject invention.
Figure 4:
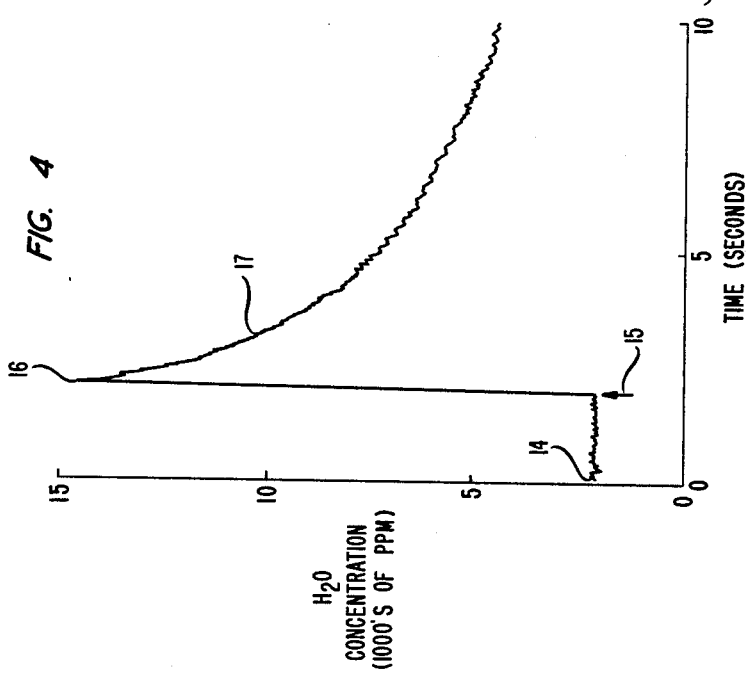
FIG. 2 through 4 are illustrative of data that relates to the subject invention.

A technique particularly adaptable for making the desired rapid measurement is described by J. Reid, J. Shewchun, B. K. Garside, E. A. Ballik, "High Sensitivity Pollution Detection Employing Tunable Diode Lasers," in *Applied Optics,* 17, pp. 300–307 (1978) and J. Reid, M. El-Sherbiny, B. K. Garside, E. A. Ballik, "Sensitivity Limits of Tunable Diode Laser Spectrometer, with Application to the Detection of NO$_2$ at the 100-ppt Level," in *Applied Optics,* 19, pp. 3349–3354 (1980), as applied to measurements of SO$_2$ and NO$_2$ concentrations in a continuous flow. This technique as adapted to the subject invention is described by P. R. Bossard and J. A. Mucha, "Dynamic Measurement of the Water Vapor Content of Integrated Circuit Packages Using Derivative Infrared Diode Laser Spectroscopy," in *IEEE Proceedings of the* 19th Annual Reliability Physics Symposium (IEEE Inc., New York, 1981), page 60. The inventive process involves impacting the sample with a source of energy having a substantial intensity at a wavelength that corresponds to an absorption band of water vapor. Typically a laser, 30, such as a PbS$_{1-x}$Se$_x$ laser, is employed to give an intensity in the range 10 μW to 1 mW at a wavelength, such as 6.05 μm, where water vapor strongly absorbs. The radiation induces absorption by the water vapor present in the sample cell, 40, and this absorption is monitored by using conventional detection devices such as a Hg-Cd-Te infrared detector, 68. At low water vapor pressures, e.g., below 1–2 mTorr (e.g., 5,000–10,000 ppm in a 0.05 cc sample sealed at 760 Torr) the second derivative of the absorption curve is proportional to the water vapor concentration. As can be seen from FIG. 4, which is a graph of the maximum of the second derivative curve as it varies with time from the instant of device puncture (point 15), the measured water vapor level for the particular sample shown is approximately 12,500 ppm after the first 0.1 second (from point 15 to point 16) and then within the next 0.9 second is substantially lowered to approximately 8500 ppm (point 17). (The puncture hole should be sufficiently large and the distance from the measurement region should be sufficiently short that adsorption and desorption effects do not significantly affect the measurement. Hole sizes of approximately 1 mm and distances of approximately 24 cm are generally adequate.)

A number of expedients are available for ensuring the quantitative measure of the inventive technique is not degraded by factors extraneous to this technique. For example, the measurement in sample cell, 40, is calibrated, and the measurement conditions are kept constant by, in one embodiment, employing a beam splitter in conjunction with a wavelength modulated source of electromagnetic radiation. One beam issuing from the beam splitter is used in the absorption measurement of the sample, and the second beam is directed through a control cell, 60, containing a fixed concentration of water vapor. The absorption in this control cell is detected by a suitable means, such as Hg-Cd-Te photodetector, 62, as the first derivative, 82, in FIG. 2, of the absorption curve vs. wavelength. The wavelength of the laser is initially set so that the lockin amplifier processing the signal from the control cell detector is nulled, i.e., is set at the zero point of the first derivative of the absorption curve vs. wavelength. (By operating the lock-in amplifier at the frequency of the wavelength modulation, the first derivative is directly obtained.) The wavelength of the electromagnetic radiation source is then automatically maintained at the center of the water vapor absorption by using the output of the lock-in amplifier as an error signal, i.e., a signal whose magnitude is equivalent to the deviation from zero. The error signal when applied to the DC level of the injection current continuously maintains a fixed emission wavelength of the PbS$_{1-x}$Se$_x$ laser. Thus, the wavelength of the laser is maintained at the wavelength corresponding to essentially maximum absorption by water vapor in the sample throughout the measurement by continuing this monitoring and adjusting process.

Figure 2:
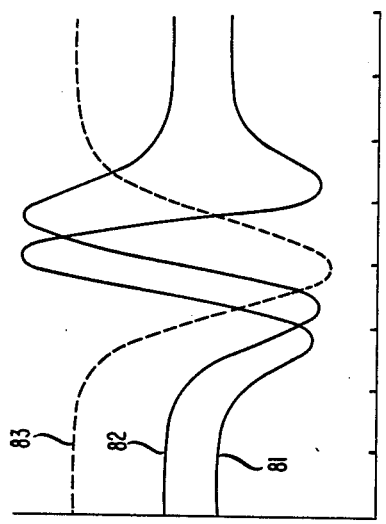

To substantially reduce the noise of the detected signal from the sample cell, 40, the wavelength of the source of electromagnetic radiation passing through this cell is modulated and phase sensitively detected. The signal detected after the electromagnetic radiation is passed through the sample cell, is processed with a lock-in amplifier tuned to twice the frequency of the wavelength modulation. Twice the frequency is employed for processing the sample signal so that the second derivative of the absorption curve vs. wavelength is measured. (See C. P. Poole, *Electron Spin Resonance; A Comprehensive Treatise on Experimental Techniques,* Chapter 10, (Interscience, New York 1967).) An example of the data obtained using this absorption analysis technique is shown in FIG. 2. The absorption spectrum (line 83 in FIG. 2) was obtained by modulating the laser beam intensity at a frequency of 400 Hz, utilizing a tuning fork chopper, phase sensitive detecting with a lock-in amplifier, and varying the DC injection current level to tune the laser between the extremes of ±0.02 cm$^{-1}$ of the center frequency at which water vapor has its peak absorption. The other traces, 82 and 81, were obtained by modulating the laser wavelength at a frequency of 1 KHz and with an amplitude approximately equal to the width of the absorption peak in the water vapor absorption curve. This modulation was accomplished by appropriately modulating the laser injection current. The line 83 in FIG. 2 indicates the absorption spectrum, line 82 corresponds to the first derivative of this curve, and line 81 corresponds to the second derivative of this curve.

The level of signal that corresponds to a particular level of water vapor is easily calibrated. For example, a sample having a known amount of water vapor is prepared from a mixture of nitrogen and water vapor in a mole ratio of, for example, 300:1. This mixture is introduced as a continuous flow into the sample cell at a pressure generally in the range 20 to 600 mTorr. This water vapor level then gives rise to a measured amplitude of the second derivative curve. By using a plurality of known samples having different water vapor levels, a calibration curve is easily established. (In fact, it is only necessary to use one known sample and to extrapolate between zero and the measured value for this sample. A plurality of samples only need be used in the first calibration to ensure that the water vapor level is in the pressure regime where the maximum of the second derivative curve yields a linear response to water vapor level.) Generally, it is desirable before a group of measurements are performed to make a single measurement on a known water vapor level sample obtained from a continuous flow gas stream of known composition. This point, when connected to the origin of the graph, yields the entire calibration curve.

In practice, although a large number of devices within a processed batch are measurable, generally a smaller representative sample is chosen. The devices (one or more) in this sample are individually measured by the inventive technique and if the sample has an acceptable level of trapped water, the entire batch is retained. Conversely, if the water vapor level is unacceptably high, the batch is discarded.

Although the invention has been described in terms of measurements of water vapor content in devices, the technique is equally applicable to the measurement of other component gases trapped in an encapsulated device. The only change necessary is that an excitation source wavelength is chosen to correspond to an absorption in the gas to be studied. Additionally, the inventive technique is also applicable to the measurement of small encapsulated gas volumes, i.e., less than 1 cc, irrespective of the vessel in which the gas is encapsulated, since the same problems in measurement encountered with trapped water in a device are present for a trapped small volume of gas in a different type of vessel. In either case, the measurement should be made in a time period less than that required for the substantial absorption of the gas on, or desorption from, the walls of the measurement chamber. This time period, as previously discussed, is determined by reference to the comparison of a continuous flow measurement to a known volume measurement of the gas.

The following example is illustrative of the process parameters employed in the subject technique.

EXAMPLE 1

A metal-lidded ceramic integrated circuit package, 52, was placed in the sample holder, 50, of the measurement apparatus. The metal lid was situated so that it was centered below a tool, 51, capable of piercing the metal within a time period of 0.01 second and leaving a 1 mm size hole. The puncturing chamber and the adjoining sample cell were sealed and evacuated to a pressure of approximately $10^{-5}$ Torr. The sample chamber was maintained at a temperature of approximately 25 degrees C. (It should be noted that it is possible to do the measurement at an elevated temperature such as 125 degrees C. By using an elevated temperature and comparing the results obtained to lower temperature measurements of another sample, it is possible to determine if a significant amount of water is adsorbed on the interior walls of the metal lidded package and to what extent such water is present.) Water vapor was introduced into the control cell, 60, until a pressure of approximately 60 mTorr as read on a thermocouple gauge was reached. At this point, the water vapor flow was discontinued and the control cell was sealed. The $PbS_{1-x}Se_x$ laser was cooled to a temperature of approximately 43.3 degrees K. Once this temperature was achieved, an injection current of approximately 0.46 amperes was applied to the diode laser. The output from the laser was split into two beams with a germanium beam splitter such that approximately 80 percent of the laser intensity was directed through the evacuated sample cell and approximately 20 percent through the control cell which contained 60 mTorr of water vapor.

The beam which was directed through the sample cell was initially amplitude modulated at 400 Hz utilizing a tuning fork chopper. The beam exiting the evacuated sample chamber was spectrally resolved by passing it through a monochromator to assure that the wavelength of the laser was approximately 6.05 um. The chopping was then discontinued.

A saw-tooth current ramp with a repetition rate of 1 KHz and an amplitude of approximately 100 milliamperes was superimposed onto the DC injection current already being applied to the laser. This produced a wavelength modulation of the laser output of approximately 0.0002 $\mu$m. The light passing through the control cell was detected using a Hg-Cd-Te detector, 62. The output of the control cell detector was monitored on an oscilloscope, 63. The DC current level of the laser and the laser temperature were adjusted until a minimum, corresponding to absorption of light by water vapor in the control cell, was observed on the oscilloscope. The saw-tooth current was then terminated and the DC injection current and the temperature were further adjusted until the absorption was maximized as observed by a corresponding deflection in the oscilloscope trace.

An injection current having a triangular shape with a 1 KHz repetition rate and an amplitude that produced approximately one-tenth of the wavelength modulation employed in the previous saw-tooth modulation was superimposed on the DC injection current. A reference signal having the same repetition rate and phase as this superimposed triangular current was applied to the lock-in amplifiers employed both in the control and sample detection electronics. The control cell lock-in amplifier, 43, was tuned at 1 KHz (the fundamental control frequency). The sample lock-in amplifier, 44, was set at 2 KHz (twice the fundamental frequency). The time constant of both lock-in amplifiers was set at 10 milliseconds. The output of the control cell detector and the sample cell detector were fed into their respective lock-in amplifiers. The DC injection level of the laser was then adjusted until the null point of the first derivative curve, the signal obtained from the control cell lock-in amplifier, was reached. After this adjustment, the output of the control cell lock-in amplifier was superimposed onto the laser injection current supplying the laser so that the wavelength of the laser beam was maintained at a wavelength which corresponded to the maximum absorption of water vapor.

Figure 3:
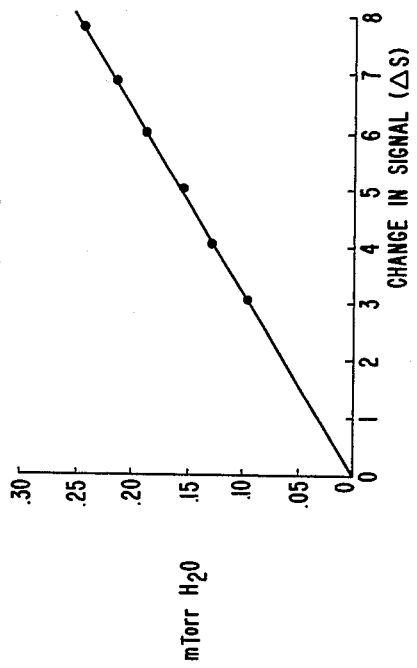

A known sample of the water vapor was prepared by passing dry nitrogen at a flow rate of approximately 100 sccm through a saturated aqueous solution of lithium chloride at room temperature. The resulting nitrogen had a water content of 3000 ppm by volume, as measured by a dew point hygrometer. The nitrogen containing the water vapor was flowed continuously through a compartment having a volume of 0.05 cc at a total pressure of one atmosphere. A leak valve in proximity to this known volume was used to initiate a flow of the nitrogen/water vapor gas into the sample cell. The leak valve was adjusted to produce a sample cell pressure of approximately 200 mTorr as monitored by a capacitance manometer. This introduction produced a detectable voltage at the output of the sample cell lock-in amplifier. The amplitude of the triangular modulation injection current was then adjusted until the voltage output from the sample cell lock-in amplifier was maximized. The leak valve was then adjusted to produce a partial pressure of 60 mTorr in the sample cell and the output of the sample cell lock-in amplifier was fed to a high-speed digital voltmeter, 46. The output of the lockin amplifier was also applied to a recorder, 47, and the signal was displayed as a function of time. The output of the recorder was monitored until it reached a stable value and the pressure and signal level were noted. The pressure in the sample cell was adjusted several times and after each adjustment the final stable value on the recorder and the pressure were noted. A calibration curve, FIG. 3, was produced utilizing the values of the water vapor content in the nitrogen as read on the dew point hygrometer, cell pressures, and the stable values obtained at each of these cell pressures. The 60 mTorr values were taken as a reference and the change in signals shown in FIG. 4 refers to the difference in signal and pressure from this reference level. Using this calibration, signal levels were directly assigned to an absolute partial pressure of water vapor in the sample cell.

The leak valve was closed and the sample chamber was evacuated to a pressure of less than $10^{-5}$ Torr. Periodically the sample cell was isolated from the vacuum pumps and the output of the sample cell lock-in amplifier was monitored with time. Typically, non-zero signals such as shown between point 14 and point 15 in FIG. 4 were observed after the cell was sealed. These signals corresponded to desorption of water from the sample cell walls. This procedure was continued until the rate of change of the desorption signal over a 5 second time interval after isolating the cell was no greater than $1 \times 10^{-5}$ Torr/second.

The cell was evacuated to a pressure of less than $1 \times 10^{-5}$ Torr and sealed. The known volume which had been continuously in contact with the nitrogen/water vapor gas was quickly isolated from the flow, trapping an aliquot of gas, and within 0.1 second this aliquot was introduced into the sealed sample cell. The total pressure in the cell from the introduction of this aliquot was measured using a capacitance manometer. The water vapor level measured as the transient part of the signal (the part of the signal similar to that between point 15 and point 16 in FIG. 4) was quantitated utilizing this data and the calibration curve. The value for the water vapor content obtained for the known volume water vapor sample and the value obtained using the hygrometor to measure the water content of the flowing gas from which the aliquot was taken agreed to within 1 percent.

The sample chamber was again evacuated and the zero level output of the lock-in amplifier was recorded. The leak valve was again opened to admit a continuous flow of the known nitrogen/water vapor gas into the sample cell and adjusted so the pressure indicated by the capacitance manometer was identical to that observed during the aliquot measurement. The signal level from the sample cell lock-in amplifier was recorded and this level was within 1 percent of the level recorded as the transient signal in the aliquot measurement. This indicated the measurement time, and sampling times were sufficiently short to accurately measure sample moisture prior to occurrence of any significant adsorption.

The sample cell was again evacuated to a pressure of less than $10^{-4}$ Torr and sealed. The metal lid on the integrated circuit package was punctured. The capacitance manometer was employed to measure the total pressure in the cell produced from the puncturing of the device. The output of the sample cell lock-in amplifier was employed with the calibration curve to determine the absolute amount of water present in this sample. The measured water vapor level was $1.39 \times 10^{-2}$ mTorr and the measured total pressure was 95.5 mTorr. These values yield a water vapor concentration in the encapsulated device of 146 ppm by volume. (The ratio of the absolute partial pressure of water vapor in the cell to the total pressure in the cell after opening the encapsulated device is the concentration.) Further measurements were made on various samples and the accuracy of these measurements were maintained by periodically measuring the known volume to assure that it did not deviate from the continuous flow values.

What is claimed is:

1. A process comprising the steps of (1) choosing a representative sample of devices from a batch of devices (2) measuring the encapsulated water vapor present in said representative sample of devices and (3) accepting said batch if said measured water vapor is less than a chosen value characterized in that from the instant that said water vapor is freed from said device the measurement that determines said water vapor level is made in a time period less than the time required for significant adsorption interaction of water with the walls of the measurement chamber.

2. The process of claim 1 wherein said measurement chamber is glass and said time period is 0.1 second.

3. The process of either claim 1 or 2 wherein said measurement depends on the absorption of infrared electromagnetic radiation.

4. A process comprising the steps of freeing a gas sample of less than 1 cc from a vessel and measuring the presence of a component of said gas characterized in that from the instant said gas is freed from said vessel the measurement that determines said component level is made in a time period that is less than the time required for substantial adsorption interaction of said gas with the walls of the measurement chamber.

5. The process of claim 4 wherein said gas is water vapor.

6. The process of claim 4 wherein said vessel is an encapsulated device.

* * * * *